United States Patent [19]
Kroll et al.

[11] Patent Number: 5,314,448
[45] Date of Patent: May 24, 1994

[54] PROCESS FOR DEFIBRILLATION PRETREATMENT OF A HEART

[75] Inventors: Mark W. Kroll, Minnetonka; Theodore P. Adams, Edina, both of Minn.

[73] Assignee: Angeion Corporation, Plymouth, Minn.

[21] Appl. No.: 783,763

[22] Filed: Oct. 28, 1991

[51] Int. Cl.$^5$ .............................. A61N 1/39
[52] U.S. Cl. ....................................... 607/5
[58] Field of Search .................. 128/419 D

[56] References Cited

U.S. PATENT DOCUMENTS 4,637,397 1/1987 Jones et al. ................ 128/419

OTHER PUBLICATIONS

J L Prevost and F Batelli, "Sur quelques effets des descharges electriques sur le couer des mammifers," *Comptes rendus hebdomadaires des seances de l'Academie des sciences*, vol. 129, pp. 1267, 1899.

R A Winkle, R H Mead, M A Ruder, et al., "Long-term outcome with the implantable cardioverter-defibrillator," *J. am Coll Cardiol.*, vol. 13, pp. 1353-1989.

M H Lehman, S Saksena, "Implantable cardioverter-defibrillators in cardiovascular practice: Report of the policy conference of the North American Society of Pacing and Electrophysiology," *PACE*, vol. 14, pp. 969-979, Jun. 1991.

R A Winkle, "State-of-the-Art of the AICD," *PACE*, vol. 14, pp. 961-966, May 1991 pt II.

N G Tullo, S Saksena, R B Krol, "Technological improvements in future implantable defibrillators,"]*CARDIO*, vol. , pp. 107-111, May 1990.

D P Zipes, J Fischer, R M King, et al, "Termination of ventricular fibrillation in dogs by depolarizing a critical amount of myocardium," *Am J Cardiol.*, vol. 36, pp. 37-44, Jul. 1975.

P S Chen, N Shibata, E G Dixon, et al, "Comparison of the defibrillation threshold and the upper limit of ventricular vulnerability," *Circulation*, vol. 73 #5, pp. 102-1028, May 1986.

J E Skinner, C Carpeggiani, C E Landisman, et al., "Correlation dimension of heartbeat interval is reduced in conscious pigs by myocardial ischemia," *Circ. Res.* vol. 68, pp. 966-976, Apr. 1991.

M W Kroll and K W Fulton, "Slope filtered correlation dimension algorithm and its evaluation with pre-fibrillation heart rate data," *J Electrocardiology*, in press.

E G Dixon, A S L Tang, P D Wolf, et al, "Improved defibrillation thresholds with large contoured epicardial electrodes and biphasic waveforms," *Circulation*, vol. 76 #5, pp. 1176-1184, Nov. 1987.

Kugelberg, Jan. "Ventricular Defibrillation: a New Aspect", *Acta Chirurgica Scandinavica*, Supp. 372, Stockholm, 1967.

H A Blair, "On the intensity-time relations for stimulation by electric currents," *J Gen Physiol.*, vol. 15, pp. 709-729, 1932.

*Primary Examiner*—William E. Kamm
*Assistant Examiner*—Scott M. Getzow
*Attorney, Agent, or Firm*—Patterson & Keough

[57] ABSTRACT

The present invention is a process to apply an electrical pretreatment to a fibrillating heart that begins the process of organizing the action of the chaotically contracting myocardial cells, so that the defibrillating waveform applied after the pretreatment can accomplish its task with less energy than would otherwise be required. The same electrodes are employed for both pretreatment and defibrillation. In one preferred embodiment a long-duration, low-voltage pretreatment pulse is generated directly by battery and voltage-conversion circuitry, and is followed by the defibrillation pulse delivered from the previously charged capacitor. In variations on this embodiment, the capacitor is charged during the pretreatment pulse, or between the pretreatment and defibrillation pulses. In other preferred embodiments, pretreatment consists of a train of pulses of appreciably lower energy than the defibrillation pulse, and with inter-pulse time adjusted so that necessary capacitor recharging can be accomplished, so that the same capacitor (a component of dominant size) can be used for all pretreatment pulses and for the defibrillation pulse as well. Wide-ranging variations of pulse duration, height spacing and waveform are included, as well as selected polarity inversions.

27 Claims, 9 Drawing Sheets

PROCESS FOR DEFIBRILLATION PRETREATMENT OF A HEART

CROSS REFERENCES TO CO-PENDING APPLICATIONS

None.

BACKGROUND OF THE INVENTION

1. Field of the Invention

The present invention relates generally to defibrillation processes, and more particularly, pertains to the new process of pretreatment, especially electrically rendering the heart muscle more amenable than it would otherwise be to the influence of defibrillation waveforms.

2. Description of the Prior Art

Defibrillation, or causing the cessation of chaotic and uncoordinated contraction of the ventricular myocardium by application of an electrical voltage and current, in its most primitive form goes back to the last century. [J. L. Prevost and F. Batelli, "Spur quelques effects des descharges electriques sur le couer des mammifers", Comptes rendus hebdomadaires des sanes de l'Academie des sciences, Vol. 129, pp 1267, 1899.] The sophistication and effectiveness of defibrillation techniques has grown rapidly in recent decades. One of the most recent developments has been the practical advent of implantable defibrillation systems. [R. A. Winkle, R. H. Mead, M. A. Ruder, et al., "Long-term outcome with the implantable cardioverter-defibrillator", J Am Coll Cardiol., vol 13, pp 1353-1361, May, 1989. M. H. Lehman, S. Saksena, "Implantable cardioverter-defibrillators in cardiovascular practice: Report of the policy conference of the North American Society of Pacing and Electrophysiology", PACE, vol 14, pp 969-979, June, 1991.] With the acceptance of this technology, the new challenge is to reduce system size while preserving its effectiveness, in order to improve the patient's quality of life and to extend the range of application of such systems. [R. A. Winkle, "State-of-the-Art of the AICD", PACE, vol 14, pp 961-966, May, 1991, pt II. N. G. Tullo, S. Saksena, R. B. Krol, "Technological improvements in future implantable defibrillators", CARDIO, vol 7, pp 107-111, May, 1990.]

The next challenge, not yet met, is to develop ways to detect imminent fibrillation so that sophisticated pacing techniques may forestall its onset, thus sparing the patient the discomfort and trauma of a high-energy electrical discharge within the upper body. [J. E. Skinner, C. Carpeggiani, C. E. Landisman, et al., "Correlation dimension of heartbeat interval is reduced in conscious pigs by myocardial ischemia", Cir. Res., vol 68, pp 966-976, April, 1991. M. W. Kroll and K. W. Fulton, "Slope filtered correlation dimension algorithm and its evaluation with pre-fibrillation heart rate data", J. Electrocardiology, vol 24, January, 1992.] Until an ability to anticipate fibrillation has been achieved, it will be necessary to achieve defibrillation by passing a large current through the heart using a system such as that represented schematically in FIG. 1, the prior art. The current must be large enough to extinguish wavefronts by directly depolarizing a major portion of the myocardium. [D. P. Zipes, J. Fischer, R. M. King, et al., "Termination of ventricular fibrillation in dogs by depolarizing a critical amount of myocardium", Am Cardiol., vol 36, pp 37-44, July, 1975.] The current value must also be above the defibrillation threshold, and above an upper limit of ventricular vulnerability so that cells will not be stimulated in a fashion that causes fibrillation to commence anew. [P. S. Chen, N. Shibata, E. G. Dixon, et al., "Comparison of the defibrillation threshold and the upper limit of ventricular vulnerability", Circulation, vol. 73 #5, pp 102-1028, May, 1986.]

Figure 1:
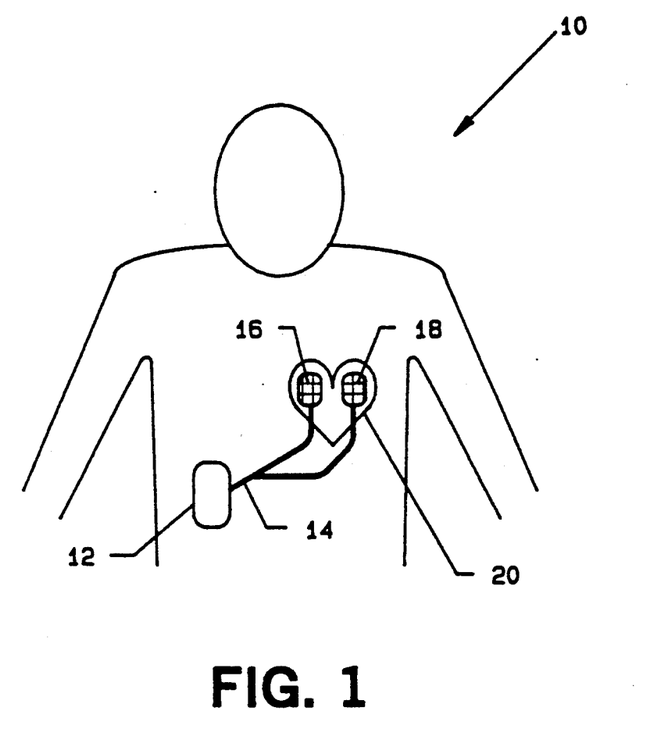
FIG 1 illustrates schematically the configuration of a conventional implantable defibrillation system.

Prior art in the broadest sense uses an arrangement like that shown schematically in FIG. 1 to deliver electrical stimulus to the heart. A typical waveform, voltage versus time, employed for defibrillation may be the monophasic waveform pictured in FIG. 2, the prior art. Typical values are a pulse duration of 7 milliseconds, a peak amplitude of 750 volts and peak current of 15 amperes, assuming electrodes that yield a heart resistance of approximately 50 ohms. A minor variation of this prior art case involved one pulse delivered between a certain pair of electrodes, and a second pulse delivered through a different pair of electrodes.

Figure 3:
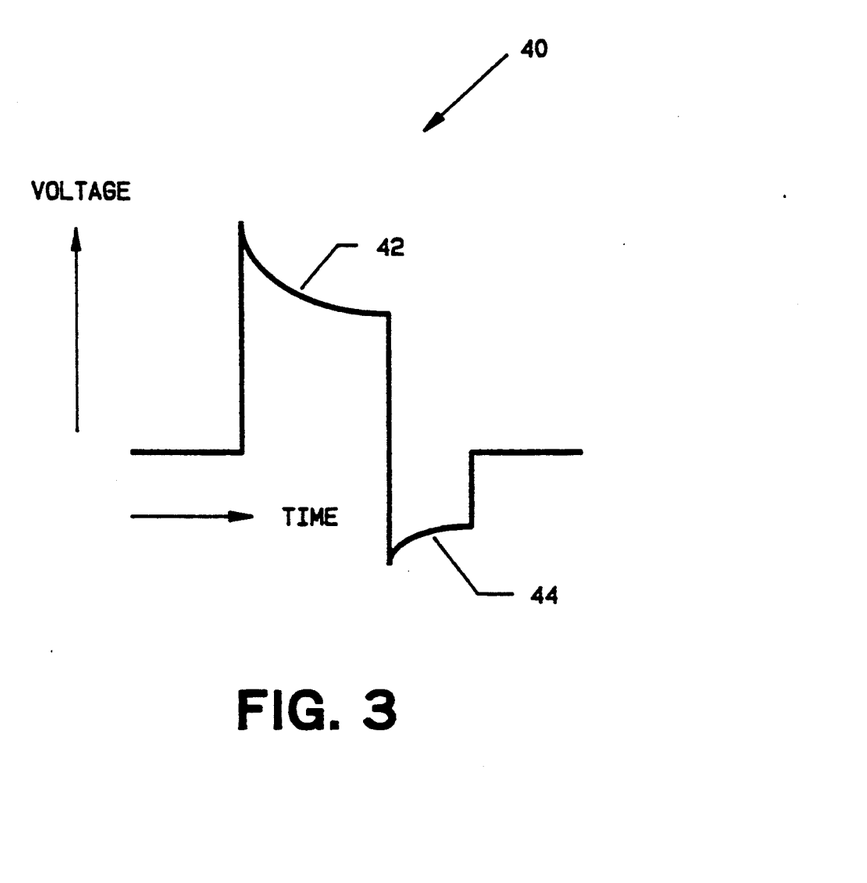
FIG. 3 illustrates schematically a conventional biphasic defibrillation pulse.

Another prior art option that shows improved results is the biphasic waveform depicted in FIG. 3, the prior art. [E. G. Dixon, A. S. L. Tang, P. D. Wolf, et al., "Improved defibrillation thresholds with large contoured epicardial electrodes and biphasic waveforms", Circulation, vol 76 #5, pp 1176-1184, Nov., 1987.] Here, the initial pulse is similar to the monophasic pulse, but a second pulse of opposite polarity is caused to follow the first immediately by a switching reversal of the capacitor.

The processes and procedures of the prior art that most nearly approach the novel feature of the present invention, however, are quite remote from it. Hence, their marginal relevance can best be appreciated by first noting the outline of the present invention.

In one embodiment of the present invention, the short-duration, high-voltage defibrillating pulse is preceded by a contiguous and same-polarity, long-duration, low-voltage waveform. In other embodiments of the present invention, a train of electrical pulses requiring little energy storage achieves temporal and spatial organization of significant portions of the heart muscle, so that a subsequent defibrillating pulse can accomplish its role using less energy than would otherwise be required. The pulse train is delivered through the large electrodes used to administer the defibrillating pulse.

The only even remotely similar methods in the prior art are these: One could argue that in the biphasic defibrillation of the prior art, the initial pulse constitutes an electrical pretreatment that improves the efficacy of the second, although several significant elements of the present invention are absent altogether in this case, particularly the train of pulses of the other embodiments. A further point of difference is that our pretreatment pulse or pulses are of significantly lower energy than the defibrillation pulse, whereas the first pulse in the biphasic waveform is usually of higher energy than the second.

Pulses delivered at a rapid rate are sometimes used in the prior art of pacing to combat tachycardia, or rapid pulse. The aim here is to "outrun" the tachycardia by administering heart-stimulating pulses at a high rate. This pulse-train case is very different from those of the present invention, however, because (1) it delivers pulses through the pacing lead rather than through the large defibrillation electrodes; (2) it employs pulse voltages in the neighborhood of 5 volts rather than several hundred volts; (3) it seeks to achieve a cessation of tachycardia rather than fibrillation; (4) its pulse train delivered through the pacing lead is never followed by a significantly stronger pulse, whereas in embodiments of the present invention, the train of pulses delivered through the defibrillation electrodes is always followed by a significantly stronger pulse.

It should be noted that the dual-pulse, single-path option was studied in the 1960s and found to yield no improvement. [Kugelberg, Jan. "Ventricular defibrillation: a new aspect", Acta Chirurgica Scandinavica, Supp 372, Stockholm, 1967.]

Another aspect of prior art is the dual-pulse process discussed above as a variation on the monophasic waveform, wherein the initial pulse could conceivably be termed "pretreatment". But this method differs fundamentally form the present invention because a different path is used for the second path in the dual-pulse method of the prior art. Other prior art is the work of Jones and Jones. [J. L. Jones and R. E. Jones, U.S. Pat. No. 4,637,397, filed May 30, 1985, and issued Jan. 20, 1987.] It employs what is essentially a biphasic pulse, followed by a comparatively low-power "healing pulse", the last having the same polarity as the first pulse. The concept of a final low-power or healing pulse is totally absent from the present invention.

Summarizing, the present invention differs from the prior art in that it uses (1) many pulses or else one or more long-duration, low-voltage pulse; (2) high-heart-rate pulse spacings greater than, for example 200 milliseconds, while the dual-pulse spacing is negligible, or the order of 1 millisecond; (3) the same pair of electrodes for all pulses; (4) one or many low-energy pulses followed by a high-energy pulse, rather than two or more pulses of comparable energy.

SUMMARY OF THE INVENTION

The general purpose of the present invention is to deliver an electrical pretreatment to the heart through the defibrillation electrodes, thus rendering it ready to respond favorably to the defibrillating waveform. An advantage of such pretreatment is that a defibrillation pulse of a given efficacy can then be achieved with less energy than that required by a heart that has not been so pretreated. Since lower total energy translates into smaller capacitor values, the smaller capacitors have smaller volume, and capacitors are a dominant factor in determining the volume of an implantable defibrillation system, the result is a reduction in system size, which is especially important in the case of implantable systems.

Figure 4:
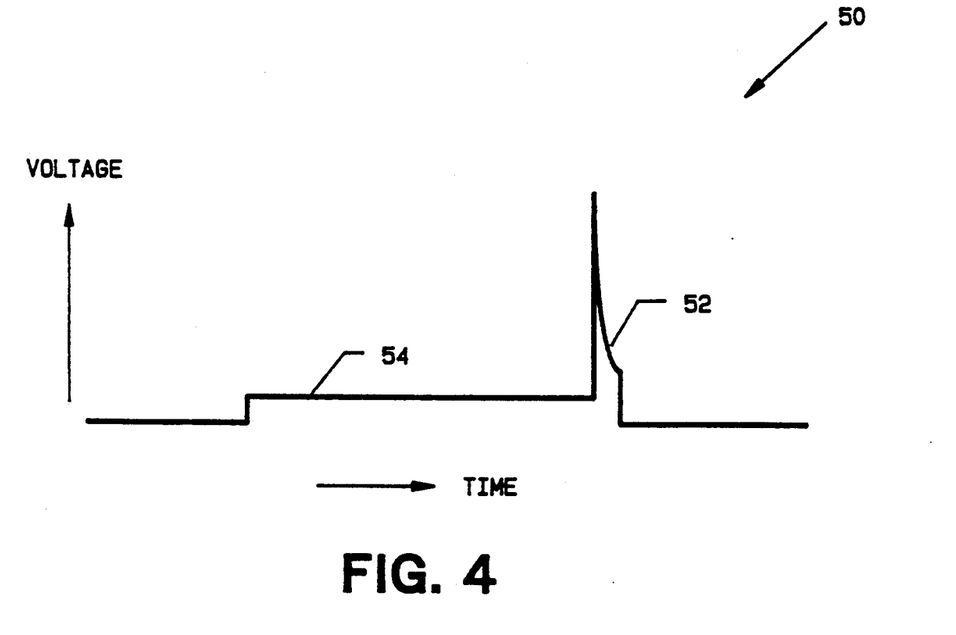
FIG. 4 illustrates schematically a conventional monophasic defibrillation pulse preceded by a long-duration, low-voltage pretreatment pulse of the present invention.

The first embodiment of the present invention applies a long-duration, low dc voltage and current to the heart through the defibrillation electrodes with the resulting overall waveform illustrated in FIG. 4. The long pulse is followed immediately by a conventional relatively short-duration, high-voltage defibrillation pulse. Typical defibrillation batteries are able to deliver 1 ampere at 6 volts, or 6 watts of power. A typical defibrillation pulse of several hundred volts is achieved by using the chopper-transformer process, thus charging a capacitor that is to be subsequently discharged through the heart muscle. Let us first assume that the full power of the battery is employed to generate the pretreatment waveform. Because the two waveforms are contiguous, it is necessary to charge the high-voltage capacitor that delivers the conventional pulse before commencing pretreatment. The initial low-voltage waveform employs the full power of the 6-W defibrillation battery involving current and voltage that can be calculated as follows:

If one assumes at 67% efficiency for the conversion from 6V to a higher voltage, then one has 4W available for delivery to the heart. Let one also assume that the resistance interposed by the heart between the pair of large-area electrodes employed for defibrillation is approximately 50 ohms. Then eliminate current I from Ohm's law, $V = IR$, where V is voltage in volts and R is resistance in ohms by using the basic power relation, $P = IV$, where P is power in watts. The result is:

$$V = \sqrt{(PR)} = \sqrt{[(4 \text{ W})(50 \text{ ohms})]} = 14 \text{ V} \quad \text{Eq. 1}$$

Using Ohm's law, then, the current is found to be approximately 0.28 amperes.

A significant variation on the pretreatment procedure just described in detail introduces a time interval between the end of the pretreatment pulse, and the beginning of the defibrillation pulse. The interval can vary from zero to several seconds. If it exceeds about 200 milliseconds, a new possibility is introduced. The capacitor used for delivering the defibrillation pulse can be charged during that period of time.

In another variation, one can select a pretreatment pulse that requires less than the full power of the battery, so that the battery can be used concurrently to charge the large capacitor. This eliminates the need to do the charging before beginning pretreatment, even when contiguous pulses are used, and thus represents a time saving.

In still another variation on this basic kind of pretreatment, one can choose pretreatment and defibrillation pulses of opposite polarity.

Pretreatment by means of a single pulse, as in the first preferred embodiment and its several variations, is said to increase the spatial organization of the cardiac muscle. It suppresses fibrillation in a portion of the heart's volume, thus diminishing the amount of defibrillation that must be accomplished by the final pulse. For a better appreciation of how this comes about, it will be helpful to review some of the rudiments of myocardial-cell functioning.

The details of heart-cell function and response to defibrillation procedures are known at least in outline. The myocardium comprises cylindrical muscle cells that are approximately 25 micrometers in diameter, and appreciably larger in the axial direction. The internal potential of the cell in the relaxed or diastolic state, which is the result of an ion-pump mechanism, is about 90 millivolts more negative than that of the general body fluid around the cells, the latter employed as potential reference. So little charge is required to create significant electric fields and potential differences that to an excellent approximation, the concentration of negative chlorine ions inside the cell equals the combined concentration there of positive sodium and potassium ions; the cell interior, like the external fluid, can be treated as space-charge neutral for analytic purposes.

It is a property of this membrane that chlorine ions can pass through it freely, but that the positive ions cannot. In the thin membrane that constitutes the cell wall, there exists a radially symmetric and inward-directed electric field. As a result, there is an outward flow of negatively-charged chlorine through the mechanism of drift in the electric field. But in this commonplace physical situation, there is a countervailing diffusion of chlorine ions inward, and the two transport mechanisms balance precisely in the present polarized state of the cell.

When the cell is triggered by a neighboring cell in the normal operation of the heart, however, the irreversible process of depolarization takes place. Waves of depolarization, and hence contraction, pass through the muscle. Depolarization involves the opening of "sodium channels" through the membrane, permitting enough sodium ions to enter to bring the internal potential near zero. Depolarization can also be triggered by an externally imposed electric field, such as that applied in a defibrillation procedure. When the externally applied field exceeds approximately 100 volts per centimeter, the irreversible depolarization process begins. For a typical spacing of epicardial-patch defibrillation electrodes, this means that several hundred volts must be applied from one electrode to the other.

Figure 7A:
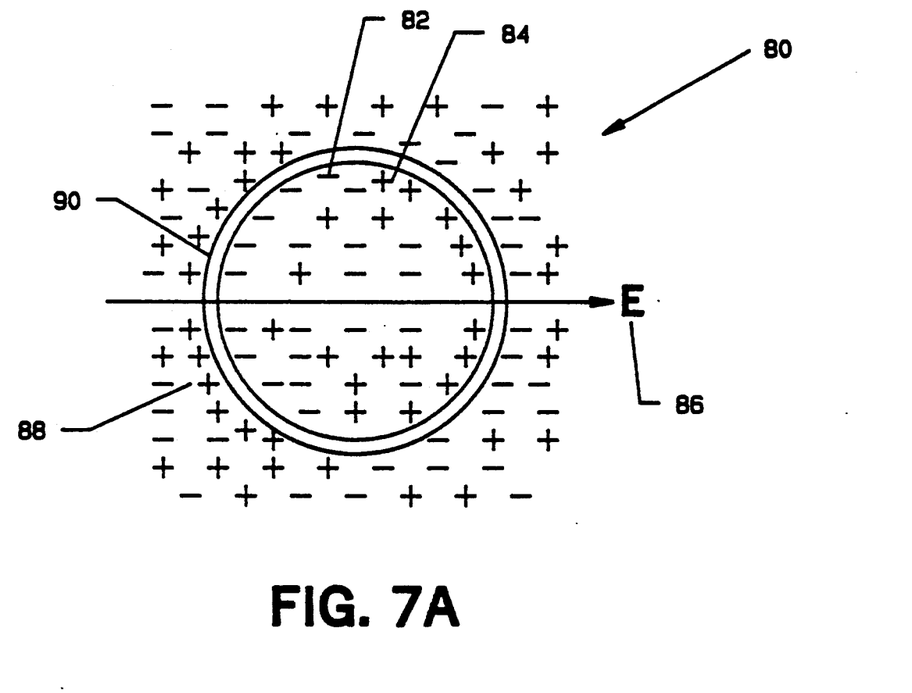
FIG. 7A illustrates schematically in cross section a myocardial cell after the application of a large electric field.

The applied field causes an internal redistribution of charges inside the cell, as represented in exaggerated fashion in FIG. 7A. Since lines of force go from positive to negative charges, it is evident that the component of internal field resulting from this charge redistribution causes the field at the center of the cell to be smaller than it would otherwise be. But depolarization triggered by the electric field virtually eliminates all space charge, that which was responsible for the radial field of the polarized cell, and brings the cell to the condition represented schematically in FIG. 7B. Thus, in defibrillation, cells are brought by brute-force means into a common state of depolarization, replacing the chaotic conditions of fibrillation.

After relaxation to the polarized state, all cells that were triggered are ready to resume normal function when triggered again by the heart's natural pacemaker, or by the medically provided substitute. The period immediately following the triggering of a cell, during which the cell is incapable of responding to another such stimulus, is known as the refractory time (or refractory period) of the cell. It is possible that some defibrillation procedures expand, or stretch out, the refractory period, thus reducing the possibility of the rapid, random and chaotic firing that characterizes fibrillation.

The cell-wall membrane prior to the firing phenomenon exhibits high resistivity, and functions as a dielectric material. This fact has invited modeling of the membrane during the period of charge buildup as a capacitor. The region of interest here is the left-hand portion of the wall represented in FIG. 7A, and so the capacitor $C_m$ in the circuit of FIG. 7C models the capacitive properties of this portion of the membrane, while the shunt resistor $R_m$ models its high (though not infinite) resistance. The physical mechanisms at work during the charging of this quasi capacitor are the rightward transport of sodium ions and potassium ions toward the exterior of the left-hand wall, and leftward transport of some chlorine ions, to charge the positive plate. At the same time, there is a redistribution of charge within the cell, delivering chlorine ions to the interior of the left-hand wall, as well as the rightward transport of potassium and some sodium ions, to charge the negative plate.

The right-hand portion of the cell wall in FIG. 7A could be modeled in similar fashion, and then internal redistribution of charge that occurs within the cell would be analogous to the charge redistribution that occurs on the two interior "isolated" plates of two capacitors when the capacitors are charged in series. The difference, of course, is that those isolated plates are normally uncharged at the start of the process in the capacitor case, whereas the cell interior is negatively charged in the muscle-cell case.

If the transmembrane voltage shift required to bring the cell to the trigger threshold is $\Delta V$, then the dc conduction current through the membrane at the threshold voltage will be given by $$I_o = \Delta V / R_m \qquad \text{Eq. 2}$$

There will also be a displacement current passing through the capacitor, this being identically equal in magnitude to the time rate of change of a real charge density on one of the "plates" of the quasi capacitor; when charge density increases, the displacement current has the same direction as the electric field, and when it decreases, the opposite direction.

As the capacitor charges and transmembrane voltage changes, current through $R_m$ changes. If the rectangular voltage pulse applied to do the charging has infinite length, then it need only deliver a current infinitesimally larger than $I_0$. But, if the pulse has the finite duration $t_p$, then a higher current is needed, given according to the model by:

$$I = I_o / [1 - \exp(-t_p / R_m C_m)] \qquad \text{Eq. 3}$$

[H. A. Blair, "On the intensity-time relations for stimulation by electric currents", *J Gen Physiol*, vol 15, pp 709-729, 1932.]

After this review of myocardial-cell triggering, let us turn to the purpose of the single-pulse electrical pretreatment that was described above, along with several variations of the basic procedure. This kind of pretreatment is said to increase the spatial organization of cells in the cardiac muscle. The electric field associated with this current is largest in the regions near the electrodes, where the lines of force in one case diverge and in the other, converge, as do the current "stream lines". In at least these regions, then, cessation of fibrillation is achieved even by the relatively low current and voltage of the pretreatment pulse. The defibrillation pulse, therefore, need only accomplish its mission in the balance of the heart muscle. This constitutes a gain. A statistical factor enters into defibrillation, and having fewer cells in need of electrical alteration increases the completeness of the final result. Thus, it is believed that, after pretreatment, defibrillation can be accomplished at a given level of effectiveness or reliability by means of less capacitor-stored energy.

Figure 5:
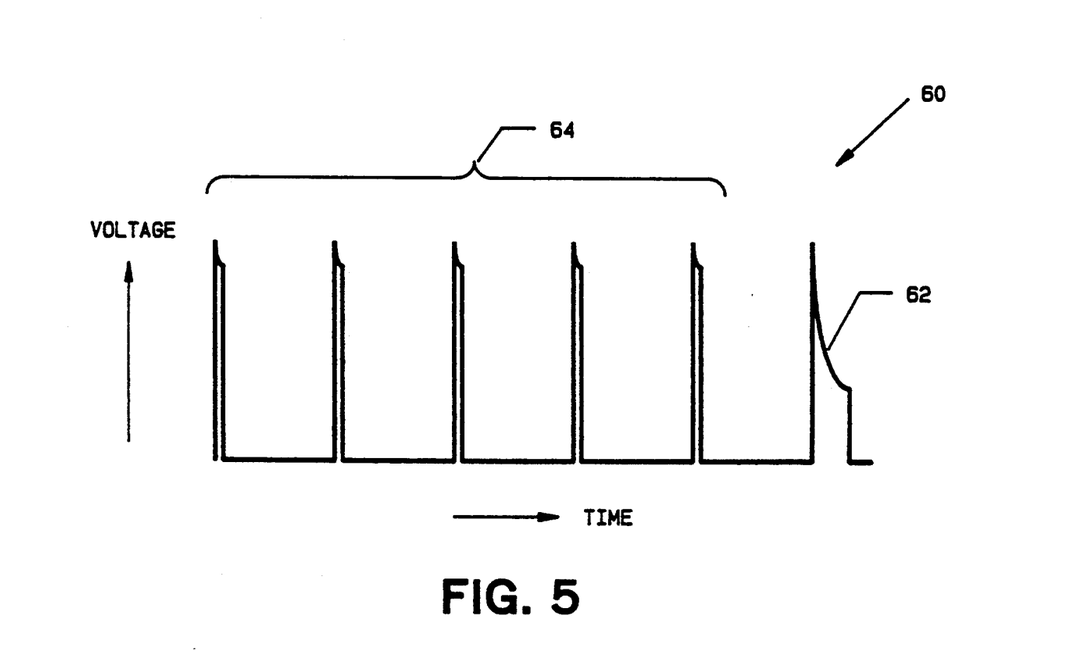
FIG. 5 illustrates schematically a conventional monophasic defibrillation pulse preceded by a train of short-duration, high-voltage pretreatment pulses of the present invention.

The second preferred embodiment of the present invention employs a train of short-duration, high-voltage pulses for pretreatment. A conventional, high-voltage defibrillation pulse follows this train at an interval equal to that between the pulses of the train. All spacings are 200 milliseconds, which corresponds to a heart rate of 300 beats per minute. This high rate is chosen because fibrillation is characterized by high rates, as well as chaotic occurrence of cell contraction, and the pretreatment must compete effectively with these conditions. The waveform, voltage versus time, employed in this pretreatment option is illustrated in FIG. 5.

To deliver both the pretreatment pulses and the main pulse, a single capacitor is used. Its value is 54 microfarads and its rating is 430 volts. The capacitor is fully charged before the pretreatment pulse train begins. Each of these pulses has a duration of 200 microseconds, which discharges the capacitor to approximately 400 volts. The pretreatment-pulse duration of 200 microseconds is chosen because it corresponds approximately to the time constant associated with a cardiac muscle cell in the relaxed state (in diastole), or the stimulation time required by a myocardial cell. The aim here is to achieve cell stimulation in the most energy-efficient manner possible, and to be able to accomplish full recharging of the capacitor during the interval between pulses.

This kind of pretreatment achieves what is describe as temporal organization of the cardiac cells, again diminishing the demands imposed on the final defibrillation pulse, and permitting the possibility of diminishing its energy requirement. It is possible to trade off pretreatment-pulse energy and spacing about the values just cited as typical. Furthermore, it will also be possible to carry out systematic changes during the pretreatment process itself. For example, once an initial degree of synchronization has been achieved at the high rate needed to combat fibrillation, it may be desirable to slow the rate and boost the energy of each pulse in order to increase the degree of temporal coordination.

To illustrate one such possible variation in the second preferred embodiment, a third preferred embodiment of the present invention is now set forth. Each pretreatment pulse is now expanded to a duration of 2.7 milliseconds, and the peak voltage is correspondingly dropped to 170 volts, while the interpulse interval is maintained at 200 milliseconds. The result is capacitor discharge down to 63 volts at the end of a pretreatment pulse. It is still possible to recharge the capacitor during the hiatus between pulses. In 200 milliseconds, however, the capacitor cannot be fully charged back up to 430 volts for the main pulse, so the final interval must exceed 200 milliseconds.

Finally, the fourth, fifth and sixth preferred embodiments of the present invention simply substitute a biphasic defibrillation pulse for the monophasic pulse in each of the first three options set forth above.

Each of these preferred embodiments can be employed with large-surface-area electrodes. These can be epicardial-patch electrodes, or subcutaneous electrodes. Each option can also be used with endocardial electrodes.

Central elements in the present invention are the broad concept of electrical pretreatment for defibrillation, and the more specific concept of pretreatment by means of pulse trains. The latter innovation introduces several new variables into the defibrillation context. The long history of the defibrillation art encompasses a substantial content of empirical experimentation, because of the complexity of the biophysical problems and the relative recency of a basic understanding of these problems. It is for this reason that the new variables deserve enumeration and consideration, in view of the inevitable future extension of empirical examination of their relevance to defibrillation pretreatment.

The primary new variables related to a train of pulses are pulse (1) length or duration, (2) height or amplitude, (3) polarity, and (4) spacing. To this listing, one could add pulse waveform in all its detail, and it is intended here that wide-ranging waveform variations are within the scope and spirit of the present invention. The second and third preferred embodiments described above represent examples of manipulating variables one and two. It is evident that both variables can be continuously altered in the range between the two examples, as well as outside the range of both ends, so these possibilities are explicitly included in the present invention. Furthermore, variables one and two can be altered within a train, smoothly or in stepwise fashion, and monotonically or nonmonotonically, and these possibilities are likewise included.

The third variable, polarity, is represented in the examples in one choice only—the case where all pulses in the train and the defibrillation pulse have the same polarity. But again it is evident that a vast array of options arises from manipulating polarities of pulses individually, in groups, and so on, and these too are deemed to be embraced herein. Finally, in addition to the example above wherein pulse spacing monotonically increases with time, one could have a monotonic decrease, or nonmonotonic variations that are open-ended, and essentially infinite in number. Such options are also included here.

Further variations can include pulse groupings. For example, the pulses can occur in closely spaced pairs, each pair separated from the next by an interval large compared to that between the paired pulses. Furthermore, the train can consist of short pulses intermixed with longer pulses. This can be further extended to include a combination of pulses in a train and one or more pulses having the long-duration, low-voltage waveform of the first pretreatment embodiment.

One significant aspect and feature of the present invention includes the concept of electrical pretreatment of a fibrillating heart to enhance the effectiveness of a defibrillation pulse.

Another significant aspect and feature of the present invention is a reduction of the defibrillation-energy requirement through the electrical pretreatment of a fibrillating heart.

Still another significant aspect and feature of the present invention is a size reduction for implantable defibrillation systems achieved by reducing the total energy required for defibrillation by means of electrical pretreatment of a fibrillating heart.

Yet another significant aspect and feature of the present invention is an electrical pretreatment of a fibrillating heart that consists of a long, low-voltage pulse to the heart, this pulse immediately preceding and contiguous with a defibrillation pulse.

Another significant aspect and feature of the present invention is a time interval introduced between pretreatment pulse and fibrillation pulse, permitting capacitor charging for defibrillation during this interval if desired.

Still another significant aspect and feature of the present invention is a pretreatment pulse requiring less than the full power of the battery, so that the battery can be used concurrently for capacitor charging for defibrillation.

Yet another significant aspect and feature of the present invention is a pretreatment pulse of polarity opposite to that of the defibrillation pulse.

An additional significant aspect and feature of the present invention is an electrical pretreatment of a fibrillating heart that consists of a train of short-duration, high-voltage pulses immediately preceding the fibrillation pulse.

Still an additional significant aspect and feature of the present invention is an electrical pretreatment of a fibrillating heart that consists of a train of longer-duration, lower-voltage pulses immediately preceding the defibrillation pulse.

Other significant aspects and features of the present invention include a train of pretreatment pulses wherein pulse duration is varied in a predetermined fashion; a train of pretreatment pulses wherein pulse height is varied in a predetermined fashion; a train of pretreatment pulses wherein pulse polarity is varied in a predetermined fashion; a train of pretreatment pulses wherein pulse spacing is varied in a predetermined fashion; a train of pretreatment pulses wherein pulse waveform is varied in a predetermined fashion; a train of pretreatment pulses wherein pulses appear in closely spaced groupings; and a train of pretreatment pulses wherein short pulses and longer pulses are intermixed.

Another significant aspect and feature of the present invention is a process for pretreatment wherein a pulse train is combined with one or more long-duration, low-voltage waveforms.

A further significant aspect and feature of the present invention is the use of a monophasic defibrillation pulse after the electrical pretreatment of a fibrillating heart.

A still further significant aspect and feature of the present invention is the use of a biphasic defibrillation pulse after the electrical pretreatment of a fibrillating heart.

Yet another significant aspect and feature of the present invention is the charging of the defibrillation capacitor after initiation of the pretreatment process, thus saving time otherwise wasted.

Other significant aspects and features of the present invention is an electrical pretreatment of a fibrillating heart that employs the same electrodes used for administering the defibrillation pulse; employing large-surface-area electrodes; employing large epicardial-patch electrodes; or employing endocardial electrodes.

An important significant aspect and feature of the present invention is generating both pretreatment and defibrillation pulses with a single capacitor.

Having thus described the embodiments and features of the present invention, it is a principal object hereof to render a fibrillating heart more amenable to electrical defibrillation therapy by applying electrical pretreatment to the heart immediately before administering the defibrillation pulse.

One object of the present invention is to render a fibrillating heart more amenable to electrical defibrillation therapy by applying electrical pretreatment that combats the disorganization of fibrillation by enhancing the spatial organization of myocardial-cell action.

Another object of the present invention is to render a fibrillating heart more amenable to electrical defibrillation therapy by applying electrical pretreatment that combats the disorganization of fibrillation by enhancing the temporal organization of myocardial-cell action.

An additional object of the present invention is to achieve defibrillation with less energy than that required in the prior art.

A further object of the present invention is to permit realization of a smaller implantable defibrillation system than those of the prior art, through use of the smaller capacitors permitted by lower-energy defibrillation.

A still further object of the present invention is to improve the success rate in defibrillation procedures.

Yet a further object of the present invention is to generate both pretreatment and defibrillation pulses with but a single capacitor.

Still another object of the present invention is to save time otherwise wasted by charging the defibrillation capacitor after initiation of the pretreatment process.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PRIOR ART

FIG. 1 illustrates schematically a patient 10, showing the configuration of a conventional implantable defibrillation system that includes a circuitry and power unit 12, abdominally implanted, and connected by wires 14 connected to a pair of epicardial patches 16 and 18 that have been stitched to the exterior of a heart 20.

Figure 2:
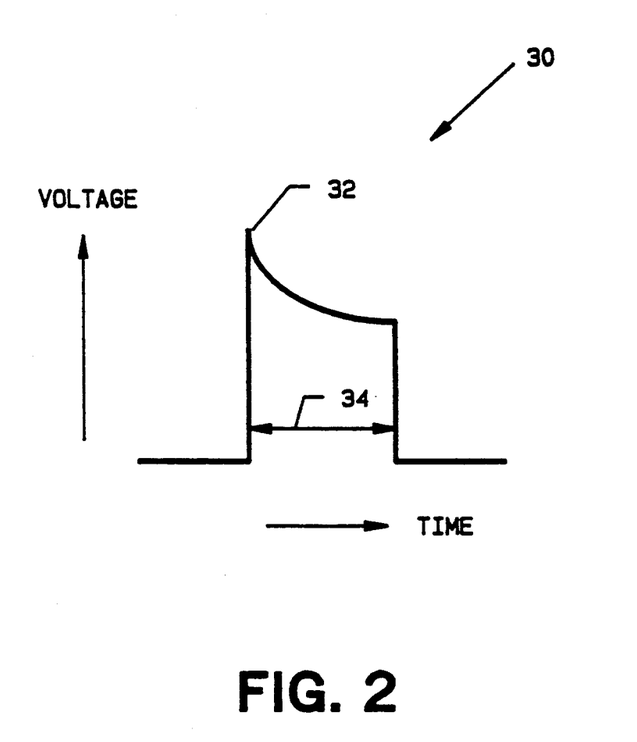
FIG. 2 illustrates schematically a conventional monophasic defibrillation pulse.

FIG. 2 illustrates schematically a conventional monophasic defibrillation pulse 30, incorporating a peak voltage 32 of 750 volts, and a duration 34 of 7 milliseconds.

FIG. 3 illustrates schematically a conventional biphasic defibrillation pulse 40, incorporating an initial pulse 42 that approximates a conventional monophasic defibrillation pulse, and an opposite-polarity pulse 44 of lesser but comparable energy.

DESCRIPTION OF THE PREFERRED EMBODIMENTS

FIG. 4 illustrates schematically the waveform 50 of a defibrillation process of the present invention including a conventional monophasic defibrillation pulse 52 preceded by a long-duration, low-voltage pretreatment pulse 54.

FIG. 5 illustrates schematically the waveform 60 of a defibrillation process of the present invention including a conventional monophasic defibrillation pulse 62 preceded by a train 64 of short-duration, high-voltage pretreatment pulses.

Figure 6:
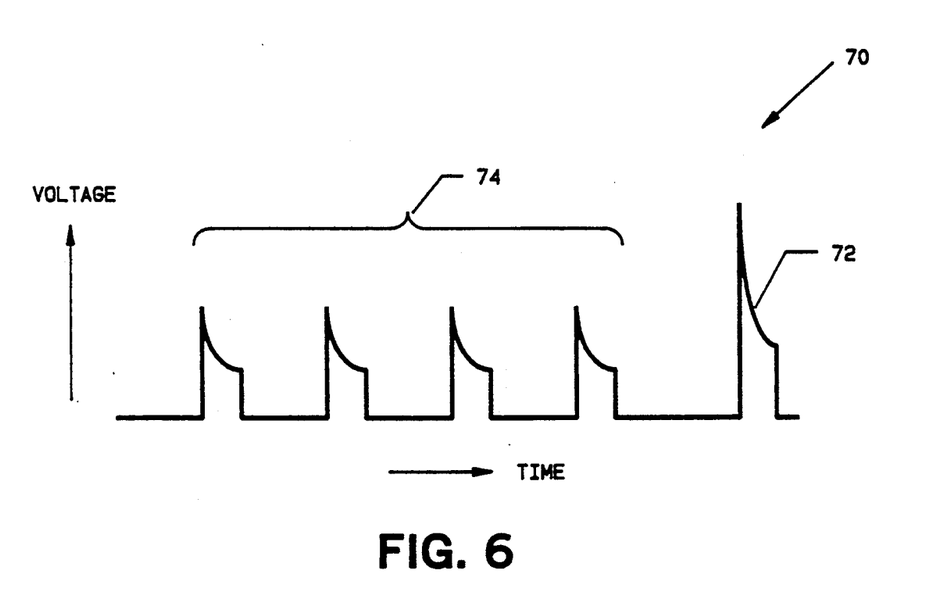
FIG. 6 illustrates schematically a conventional monophasic defibrillation pulse preceded by a train of longer-duration, lower-voltage pretreatment pulses of the present invention.

FIG. 6 illustrates schematically the waveform 70 of a defibrillation process of the present invention including a conventional monophasic defibrillation pulse 72 preceded by a train 74 of longer-duration, lower-voltage pretreatment pulses than in the previous embodiment.

FIG. 7A illustrates schematically in cross section a myocardial cell 80 with internal charges such as 82 and 84 redistributed and separated by the application of a large electric field 86, and having positive ions such as 88 pushed against the exterior wall of the cell membrane portion 90.

Figure 7B:
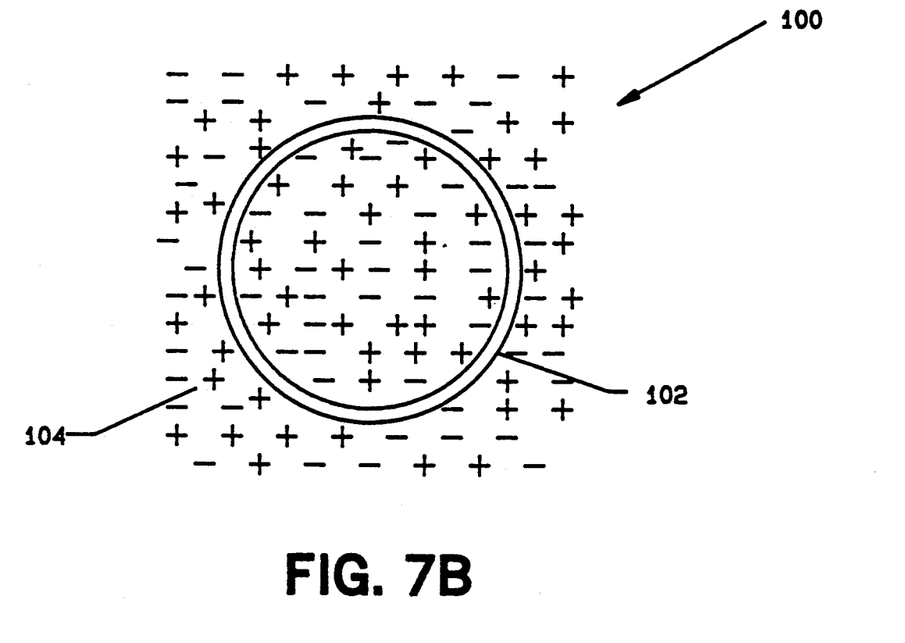
FIG. 7B illustrates schematically in cross section a myocardial cell after having been triggered by the application of a large electric field, rendering all regions essentially space-charge neutral, but after the field has been removed; and, FIG. 7C illustrates the equivalent-circuit modeling of a portion of the cell-wall membrane of a myocardial cell.

FIG. 7B illustrates schematically in cross section a myocardial cell 100 after having been triggered by the application of a large electric field, but after the field has been removed, rendering all regions essentially space-charge neutral, and causing the entry into the cell 100 through the membrane 102 of sufficient positive ions so that there are now approximately zero electrostatic potential difference from the interior of the membrane 102 to the neutral surrounding body fluid 104.

Figure 7C:
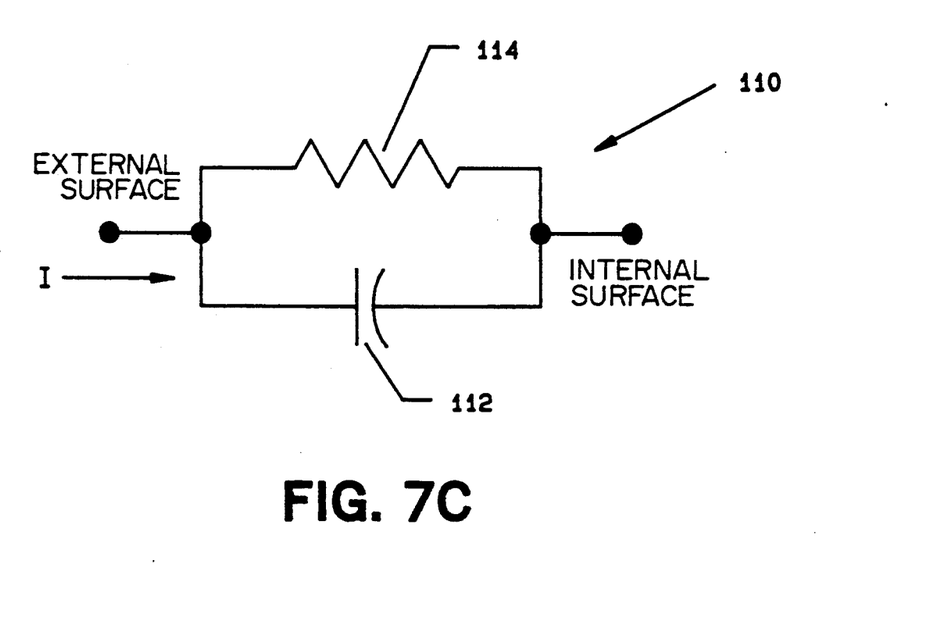

FIG. 7C illustrates an equivalent-circuit model 110 that electrically approximates the membrane or cell-wall portion 90 of FIG. 7A, inasmuch as the membrane portion 90 possess capacitive properties that can be modeled by using a capacitor 112 shunted by a resistor 114 that models the conductive or electrical-leakage properties of the membrane portion 90.

MODE OF OPERATION

In the first preferred embodiment of the present invention, the capacitor charging necessary for supplying the defibrillation waveform is done prior to the initiation of pretreatment. The pretreatment waveform consists of the application of a low dc voltage, such as 14 volts, which is derived directly from the 6-volt battery with the aid of voltage-conversion circuitry, typically chopper and transformer. The volume demands of such circuitry are small in a defibrillation system, a matter of great importance in an implantable system. The low-voltage pretreatment is applied for a time long compared to the duration of the defibrillation pulse, which is triggered precisely at the instant of discontinuing the pretreatment pulse. The pretreatment and defibrillation pulses are typically applied to the same pair of electrodes.

In the second embodiment of the present invention, the single 54-microfarad capacitor of the system is fully charged to 430 volts, and discharged to 400 volts through the heart, which takes about 200 microseconds. In the ensuing 200 milliseconds, the capacitor is recharged to 430 volts. This is the first pulse in the train of many identical pulses that now constitutes the pretreatment process. The last pulse administered by the same capacitor is stretched to 3 milliseconds, and constitutes the defibrillation pulse.

A third embodiment of the present invention employs the same general scheme as the second, and the same capacitor and electrodes, and the same interval between the pulses of the pretreatment train. This time, however, the duration of each pretreatment pulse is expanded to 2.7 milliseconds, and peak voltage is reduced to 170 volts. For the defibrillation pulse, the capacitor is fully charged to 430 volts, which requires a charging interval somewhat longer than 200 milliseconds.

In addition to the three options just cited, there are numerous variations that are within the scope and intent of the invention. In the first embodiment, a time interval can be introduced between the two pulses, or a lower-powered first pulse can be selected to permit simultaneous capacitor charging, or opposite-polarity pulses can be chosen. In the second and third embodiments involving pulse trains, one can choose extensively varied combinations of pulse length, height, polarity, spacing, waveform, and variations of all these within a given pulse train. Furthermore, stepwise or smooth variations of any of these factors can occur during the pulse train. It is also possible to have a pulse train in which pulses are grouped, or are intermixed with longer pulses, or combined with one or more long-duration, low-voltage pulses.

Various modifications can be made to the resent invention without departing from the apparent scope hereof.

We claim:

1. A process for the electrical pretreatment of a fibrillating heart comprising:
   a. at least one low-energy pretreatment pulse applied to the heart before application of a defibrillation pulse to the heart;
   b. at least one of said pretreatment pulses having a duration that is long compared to that of said defibrillation pulse and a voltage that is low compared to that of said defibrillation pulse; and
   c. said pretreatment pulses being spaced away from said defibrillation pulse by a time interval.

2. A process for the electrical pretreatment of a fibrillating heart comprising:
   a. at least one low-energy pretreatment pulse applied to the heart before application of a defibrillation pulse to the heart; and,
   b. wherein said pretreatment pulse is spaced away from said defibrillation pulse by a time interval of at least 100 milliseconds and said defibrillation pulse is a biphasic pulse.

3. A process for the electrical pretreatment of a fibrillating heart comprising:
   a. low-energy pretreatment pulses applied to the heart before application of a defibrillation pulse to the heart; and,
   b. wherein the electrical pretreatment comprises a train of said low-energy pulses with zero-voltage intervals.

4. The process of claim 3 wherein the substantially zero-voltage interval between the pulses in the train is between 100 milliseconds and 400 milliseconds.

5. The process of claim 3 wherein all substantially zero-voltage intervals between the pulses in the train are equal.

6. The process of claim 3 wherein the substantially zero-voltage intervals between the pulses in the train are variable.

7. The process of claim 3 wherein the substantially zero-voltage intervals between the pulses in the train increase monotonically in duration as the train progresses.

8. The process of claim 3 wherein the substantially zero-voltage intervals between the pulses in the train decrease monotonically in duration as the train progresses.

9. The process of claim 3 wherein the substantially zero-voltage intervals between the pulses in the train vary nonmonotonically in duration as the train progresses.

10. The process of claim 3 wherein a capacitor is utilized for generating the pretreatment and defibrillation waveforms.

11. The process of claim 3 wherein each pulse of the train has a duration that is short compared to that of a conventional monophasic defibrillation pulse and a voltage that is comparable to that of a conventional monophasic defibrillation pulse.

12. The process of claim 3 wherein each pulse of the train has a duration that is one-tenth to one-half that of a conventional monophasic defibrillation pulse and a voltage that is one-tenth to one-half that of a conventional monophasic defibrillation pulse.

13. The process of claim 3 wherein the pretreatment increases the temporal organization of the myocardial cells.

14. The process of claim 3 comprising a monophasic defibrillation pulse.

15. The process of claim 3 comprising a biphasic defibrillation pulse.

16. The process of claim 3 wherein a capacitor is utilized for generating the pretreatment and defibrillation waveforms.

17. The process of claim 3 comprising pulses grouped in clusters of at least two.

18. The process of claim 3 comprising short pulses intermixed with longer pulses.

19. The process of claim 3 comprising a pulse train combined with one or more long-duration, low-voltage pulses.

20. The process of claim 3 wherein at least one of these pulse-train attributes is varied within the duration of the train: pulse length, pulse height, pulse spacing, or pulse waveforms.

21. The process of claim 20 wherein the variation is stepwise.

22. The process of claim 20 wherein the variation is smooth.

23. The process of claim 20 wherein the variation is monotonic.

24. The process of claim 20 wherein the variation is nonmonotonic.

25. The process of claim 20 with the added variation of pulse polarity.

26. A process for the electrical pretreatment of a fibrillating heart comprising:
   a. at least one low-energy pretreatment pulse applied to the heart before application of a defibrillation pulse to the heart, wherein said pretreatment pulse is spaced away from the defibrillation pulse by a time interval of sufficient length to permit recharging of a defibrillation capacitor; and
   b. at least one pulse having a duration that is long compared to that of said defibrillation pulse and a voltage that is low compared to that of said defibrillation pulse.

27. A process for the electrical pretreatment of a fibrillating heart comprising:
   a. at least one low-energy pretreatment pulse applied to the heart before application of a defibrillation pulse to the heart, wherein said pretreatment pulse is spaced away from the defibrillation pulse by a time interval; and
   b. at least one pulse having a duration that is long compared to that of said defibrillation pulse and a voltage that is low compared to that of said defibrillation pulse.

* * * * *